US012752115B2

(12) United States Patent
Shrivastav et al.

(10) Patent No.: US 12,752,115 B2
(45) Date of Patent: Oct. 6, 2026

(54) NEUROMODULATION FOR TREATMENT OF NEONATAL CHRONIC HYPERINSULINISM

(71) Applicant: Medtronic, Inc., Minneapolis, MN (US)

(72) Inventors: Maneesh Shrivastav, Blaine, MN (US); Shaileshkumar V. Musley, Brooklyn Park, MN (US); Kanthaiah Koka, Valencia, CA (US); Steven M. Goetz, North Oaks, MN (US); Suryakiran Vadrevu, Santa Clarita, CA (US); Rebecca K. Gottlieb, Culver City, CA (US); David John Miller, Austin, TX (US); Leonid M. Litvak, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 266 days.

(21) Appl. No.: 18/131,576

(22) Filed: Apr. 6, 2023

(65) Prior Publication Data

US 2023/0355976 A1 Nov. 9, 2023

Related U.S. Application Data

(60) Provisional application No. 63/342,967, filed on May 17, 2022, provisional application No. 63/342,945,
(Continued)

(51) Int. Cl.
*A61N 1/36* (2006.01)
*A61B 5/00* (2006.01)
(Continued)

(52) U.S. Cl.
CPC ...... *A61N 1/36053* (2013.01); *A61B 5/14532* (2013.01); *A61B 5/7435* (2013.01);
(Continued)

(58) Field of Classification Search
CPC ...... A61N 1/3605; G16H 30/20; G16H 40/63; G16H 40/67; G16H 20/30; G16H 50/20;
(Continued)

(56) References Cited

U.S. PATENT DOCUMENTS 4,602,624 A 7/1986 Naples et al.
4,926,874 A 5/1990 Lee
(Continued)

FOREIGN PATENT DOCUMENTS

CN 101401314 4/2009
WO WO 2017/115368 7/2017
(Continued)

OTHER PUBLICATIONS

Aune et al. "Diabetes mellitus and the risk of sudden cardiac death: a systematic review and meta-analysis of prospective studies," Nutrition, Metabolism and Cardiovascular Diseases, 2018, vol. 28, pp. 543-556.
(Continued)

*Primary Examiner* — Niketa Patel
*Assistant Examiner* — Attiya Sayyada Hussaini
(74) *Attorney, Agent, or Firm* — Sheridan Ross PC

(57) ABSTRACT

A system is provided herein for stimulating an anatomical element of a patient to regulate insulin production of the patient. In some examples, the system may include a device configured to generate a current and an electrode device electrically coupled to the device. Subsequently, the device may receive instructions to apply the current to the anatomical element via a plurality of electrodes of the electrode device, where the current is configured to regulate insulin
(Continued)

production of the patient. For example, a first electrode may be configured for placement on or around a celiac vagal trunk, where the current downregulates neural activity of the celiac vagal trunk, and a second electrode may be configured for placement on or around a hepatic vagal trunk, where the current upregulates neural activity of the hepatic vagal trunk.

5 Claims, 5 Drawing Sheets

Related U.S. Application Data filed on May 17, 2022, provisional application No. 63/342,998, filed on May 17, 2022, provisional application No. 63/339,049, filed on May 6, 2022, provisional application No. 63/339,101, filed on May 6, 2022, provisional application No. 63/339,160, filed on May 6, 2022, provisional application No. 63/339,154, filed on May 6, 2022, provisional application No. 63/339,024, filed on May 6, 2022, provisional application No. 63/339,304, filed on May 6, 2022, provisional application No. 63/339,136, filed on May 6, 2022, provisional application No. 63/338,794, filed on May 5, 2022, provisional application No. 63/338,806, filed on May 5, 2022, provisional application No. 63/338,817, filed on May 5, 2022.

(51) Int. Cl.

| | |
|---|---|
| ***A61B 5/145*** | (2006.01) |
| ***A61B 17/135*** | (2006.01) |
| ***A61N 1/02*** | (2006.01) |
| ***A61N 1/05*** | (2006.01) |
| ***A61N 1/372*** | (2006.01) |
| ***G16H 10/40*** | (2018.01) |
| ***G16H 20/17*** | (2018.01) |
| *A61B 17/00* | (2006.01) |

(52) U.S. Cl.

CPC .......... *A61B 17/1355* (2013.01); *A61N 1/025* (2013.01); *A61N 1/0507* (2013.01); *A61N 1/0551* (2013.01); *A61N 1/0556* (2013.01); *A61N 1/0558* (2013.01); *A61N 1/36007* (2013.01); *A61N 1/3606* (2013.01); *A61N 1/36132* (2013.01); *A61N 1/36135* (2013.01); *A61N 1/36139* (2013.01); *A61N 1/36146* (2013.01); *A61N 1/36171* (2013.01); *A61N 1/36185* (2013.01); *A61N 1/37247* (2013.01); *G16H 10/40* (2018.01); *G16H 20/17* (2018.01); *A61B 2017/00867* (2013.01); *A61N 1/3605* (2013.01)

(58) Field of Classification Search

CPC .... G16H 50/70; A61B 5/0022; A61B 5/4836; A61B 5/01; A61B 5/02438; A61B 5/053; A61B 5/1123; A61B 5/14551; A61B 5/392; A61B 2562/0219; A61B 5/1118; A61B 5/686; A61B 7/00; A61B 7/008

See application file for complete search history.

(56) References Cited

U.S. PATENT DOCUMENTS

| | | | | |
|---|---|---|---|---|
| 5,487,756 | A | 1/1996 | Kallesoe et al. | |
| 6,572,543 | B1 | 6/2003 | Christopherson et al. | |
| 7,069,078 | B2 | 6/2006 | Houben | |
| 7,369,897 | B2 | 5/2008 | Boveja et al. | |
| 7,702,386 | B2 | 4/2010 | Dobak et al. | |
| 7,818,069 | B2 | 10/2010 | Colborn et al. | |
| 8,244,347 | B2 | 8/2012 | Lozano | |
| 8,340,760 | B2 | 12/2012 | Dobak, III | |
| 8,428,719 | B2 | 4/2013 | Napadow | |
| 8,868,211 | B2 | 10/2014 | Durand et al. | |
| 9,033,969 | B2 | 5/2015 | Azamian et al. | |
| 9,833,621 | B2 | 12/2017 | Levine | |
| 9,937,344 | B2 | 4/2018 | Starkebaum et al. | |
| 9,974,955 | B2 | 5/2018 | Thornton et al. | |
| 10,292,596 | B2 | 5/2019 | Shadforth et al. | |
| 10,750,994 | B2 | 8/2020 | Annoni et al. | |
| 10,850,100 | B2 | 12/2020 | Cakmak | |
| 10,856,926 | B2 | 12/2020 | Azamian et al. | |
| 11,191,966 | B2 | 12/2021 | Wah | |
| 2006/0282145 | A1 | 12/2006 | Caparso et al. | |
| 2008/0039904 | A1 | 2/2008 | Bulkes et al. | |
| 2008/0046055 | A1 | 2/2008 | Durand et al. | |
| 2008/0154177 | A1 | 6/2008 | Moubayed et al. | |
| 2008/0215101 | A1 | 9/2008 | Rezai et al. | |
| 2008/0234780 | A1 | 9/2008 | Smith et al. | |
| 2009/0254143 | A1 | 10/2009 | Tweden et al. | |
| 2010/0210955 | A1 | 8/2010 | Forsell | |
| 2011/0147046 | A1 | 6/2011 | Bonde et al. | |
| 2011/0264116 | A1 | 10/2011 | Kocur et al. | |
| 2011/0301408 | A1 | 12/2011 | Augarten | |
| 2013/0165994 | A1 | 6/2013 | Ternes et al. | |
| 2014/0074188 | A1 | 3/2014 | Armstrong et al. | |
| 2014/0228900 | A1 | 8/2014 | Osorio | |
| 2015/0045850 | A1 | 2/2015 | Bork et al. | |
| 2015/0148869 | A1 | 5/2015 | Dorvall et al. | |
| 2015/0328464 | A1 | 11/2015 | Henry et al. | |
| 2015/0374296 | A1 | 12/2015 | Baru et al. | |
| 2016/0114165 | A1 | 4/2016 | Levine et al. | |
| 2017/0021174 | A1* | 1/2017 | Thornton ........... | A61N 1/36007 |
| 2017/0164876 | A1 | 6/2017 | Hyde et al. | |
| 2018/0085580 | A1 | 3/2018 | Perez et al. | |
| 2018/0104500 | A1 | 4/2018 | Blum | |
| 2018/0125689 | A1 | 5/2018 | Perez et al. | |
| 2018/0303648 | A1 | 10/2018 | Mische | |
| 2018/0326162 | A1 | 11/2018 | Bral | |
| 2019/0125226 | A1 | 5/2019 | Koya | |
| 2019/0125227 | A1 | 5/2019 | Koya et al. | |
| 2019/0174891 | A1 | 6/2019 | Nieves | |
| 2019/0175915 | A1 | 6/2019 | Brill et al. | |
| 2019/0192851 | A1 | 6/2019 | Possover | |
| 2019/0329040 | A1 | 10/2019 | Mustakos et al. | |
| 2019/0339224 | A1 | 11/2019 | Bhavaraju et al. | |
| 2020/0206496 | A1 | 7/2020 | Meng | |
| 2020/0230400 | A1 | 7/2020 | Shepard et al. | |
| 2020/0230412 | A1 | 7/2020 | Rondoini et al. | |
| 2020/0254259 | A1 | 8/2020 | Libbus et al. | |
| 2021/0146136 | A1* | 5/2021 | Waataja .............. | A61N 1/3606 |
| 2021/0244949 | A1 | 8/2021 | Soin | |
| 2021/0275819 | A1 | 9/2021 | Boor et al. | |
| 2021/0290949 | A1 | 9/2021 | Holinski | |
| 2022/0062621 | A1 | 3/2022 | Hogg | |
| 2022/0193414 | A1 | 6/2022 | Waataja et al. | |
| 2023/0000447 | A1 | 1/2023 | Mikhno | |

FOREIGN PATENT DOCUMENTS

| | | |
|---|---|---|
| WO | WO 2020/214982 | 10/2020 |
| WO | WO 2020/252428 | 12/2020 |
| WO | WO 2020/254795 | 12/2020 |
| WO | WO 2021/119741 | 6/2021 |

OTHER PUBLICATIONS

Bergner et al. "Diabetes mellitus and sudden cardiac death," Cardiology Journal, 2010, vol. 17, No. 2, pp. 117-129.

Chow et al. "Risk of Cardiac Arrhythmias During Hypoglycemia in Patients with Type 2 Diabetes and Cardiovascular Risk," Diabetes, May 2014, vol. 63, No. 5, pp. 1738-1747.

Hanefeld et al. "Hypoglycemia and Cardiovascular Risk: Is There a Major Link?" Diabetes Care, 2016, vol. 39, Suppl. 2, pp. S205-S209.

(56) References Cited

OTHER PUBLICATIONS

Hirotani et al. "Carbon Nanotube Thin Films for High-Performance Flexible Electronics Applications," Topics in Current Chemistry, Jan. 2019, vol. 377, No. 1, Article No. 3.
Hsieh et al. "The enigma of the dead-in-bed syndrome: challenges in predicting and preventing this devastating complication of type 1 diabetes," Journal of Diabetes and its Complications, 2014, vol. 28, pp. 585-587.
Jones et al. "Neuromodulation using ultra low frequency current waveform reversibly blocks axonal conduction and chronic pain," Science Translational Medicine, Aug. 2021, vol. 13, No. 608, article eabg9890.
Jovanov et al. "Sensors and Systems for Obesity Care and Research," IEEE, 36th Annual International Conference of the IEEE Engineering in Medicine and Biology Society, Aug. 2014, pp. 3188-3191.
Murastov et al. "Flexible and water-stable graphene-based electrodes for long-term use in bioelectronics," Biosensors and Bioelectronics, Oct. 2020, vol. 166, Article 112426.
Shapiro et al. Pudendal Nerve Block by Low-Frequency (≤1 kHz) Biphasic Electrical Stimulation, Neuromodulations, Aug. 2021, vol. 24, No. 6, pp. 1012-1017.
Tancredi et al. "Excess Mortality among Persons with Type 2 Diabetes," The New England Journal of Medicine, 2015, vol. 373, pp. 1720-1732.
Yi et al. "The role of the autonomic nervous liver innervation in the control of energy metabolism," Biochimica et Biophysica Acta, Apr. 2010, vol. 1802, No. 4, pp. 416-431.
Zaccardi et al. "Diabetes mellitus and risk of sudden cardiac death," International Journal of Cardiology, Dec. 2014, vol. 177, No. 2, pp. 535-537.
International Search Report and Written Opinion for International (PCT) Patent Application No. PCT/US2023/065510, dated Jul. 11, 2023 10 pages.
International Search Report and Written Opinion for International (PCT) Patent Application No. PCT/US2023/065428, dated Jul. 20, 2023 12 pages.
U.S. Appl. No. 18/131,500, filed Apr. 6, 2023.
U.S. Appl. No. 18/131,513, filed Apr. 6, 2023.
U.S. Appl. No. 18/131,542, filed Apr. 6, 2023.
U.S. Appl. No. 18/131,555, filed Apr. 6, 2023.
U.S. Appl. No. 18/131,592, filed Apr. 6, 2023.
U.S. Appl. No. 18/132,186, filed Apr. 7, 2023.
U.S. Appl. No. 18/131,614, filed Apr. 6, 2023.
U.S. Appl. No. 18/132,204, filed Apr. 7, 2023.
U.S. Appl. No. 18/132,219, filed Apr. 7, 2023.
U.S. Appl. No. 18/132,232, filed Apr. 7, 2023.
Official Action for U.S. Appl. No. 18/131,500, dated Jan. 8, 2026 11 pages.
International Preliminary Report on Patentability for International (PCT) Patent Application No. PCT/US2023/065510, dated Nov. 14, 2024 7 pages.
International Preliminary Report on Patentability for International (PCT) Patent Application No. PCT/US2023/065428, dated Nov. 14, 2024 8 pages.
Official Action for European Patent Application No. 23721235.2, dated Oct. 23, 2025, 4 pages.
Official Action for U.S. Appl. No. 18/131,500, dated May 21, 2025 6 pages Restriction Requirement.
Official Action for U.S. Appl. No. 18/131,500, dated Jul. 28, 2025 10 pages.
Official Action for U.S. Appl. No. 18/131,513, dated Jun. 4, 2025 12 pages.
Official Action for U.S. Appl. No. 18/131,513, dated Dec. 10, 2025 11 pages.
Official Action for U.S. Appl. No. 18/131,542, dated Jul. 3, 2025 21 pages.
Official Action for U.S. Appl. No. 18/131,542, dated Oct. 24, 2025 24 pages.
Official Action for U.S. Appl. No. 18/131,555, dated Jul. 24, 2025 6 pages Restriction Requirement.
Official Action for U.S. Appl. No. 18/131,555, dated Aug. 14, 2025 14 pages.
Official Action for U.S. Appl. No. 18/131,555, dated Oct. 24, 2025 16 pages.
Official Action for U.S. Appl. No. 18/131,592, dated Jun. 11, 2025 15 pages.
Official Action for U.S. Appl. No. 18/131,592, dated Sep. 19, 2025 19 pages.
Official Action for U.S. Appl. No. 18/132,186, dated Aug. 19, 2025 24 pages.
Official Action for U.S. Appl. No. 18/131,614, dated Sep. 17, 2025 8 pages.
Official Action for U.S. Appl. No. 18/131,614, dated Nov. 10, 2025 29 pages.
Official Action for U.S. Appl. No. 18/132,219, dated Jun. 30, 2025 16 pages.
Notice of Allowance for U.S. Appl. No. 18/132,219, dated Nov. 13, 2025 11 pages.
Official Action for U.S. Appl. No. 18/132,232, dated Jul. 17, 2025 20 pages.
Official Action for U.S. Appl. No. 18/132,232, dated Nov. 21, 2025 28 pages.
Notice of Allowance for U.S. Appl. No. 18/131,513, dated Apr. 3, 2026 8 pages.
Official Action for U.S. Appl. No. 18/131,542, dated Mar. 10, 2026 25 pages.
Official Action for U.S. Appl. No. 18/131,555, dated Mar. 12, 2026 16 pages.
Official Action for U.S. Appl. No. 18/132,186, dated Mar. 4, 2026 26 pages.
Official Action for U.S. Appl. No. 18/131,614, dated Apr. 9, 2026 11 pages.
Notice of Allowance for U.S. Appl. No. 18/132,204, dated Mar. 20, 2026 9 pages.
Official Action for U.S. Appl. No. 18/862,817, dated Jun. 3, 2026 43 pages.
Notice of Allowance for U.S. Appl. No. 18/132,204, dated Jun. 10, 2026 10 pages.

* cited by examiner

NEUROMODULATION FOR TREATMENT OF NEONATAL CHRONIC HYPERINSULINISM

CROSS REFERENCE TO RELATED APPLICATIONS

This application claims the benefit of U.S. Provisional Application No. 63/339,136, filed on May 6, 2022, entitled "Neuromodulation for Treatment of Neonatal Chronic Hyperinsulinism"; U.S. Provisional Application No. 63/338,794, filed on May 5, 2022, entitled "Systems and Methods for Stimulating an Anatomical Element Using an Electrode Device"; U.S. Provisional Application No. 63/339,049, filed on May 6, 2022, entitled "Systems and Methods for Mechanically Blocking a Nerve"; U.S. Provisional Application No. 63/338,806, filed on May 5, 2022, entitled "Systems and Methods for Wirelessly Stimulating or Blocking at Least One Nerve"; U.S. Provisional Application No. 63/339,101, filed on May 6, 2022, entitled "Neuromodulation Techniques to Create a Nerve Blockage with a Combination Stimulation/Block Therapy for Glycemic Control"; U.S. Provisional Application No. 63/342,945, filed on May 17, 2022, entitled "Neuromodulation Techniques for Treatment of Hypoglycemia"; U.S. Provisional Application No. 63/342,998, filed on May 17, 2022, entitled "Closed-Loop Feedback and Treatment"; U.S. Provisional Application No. 63/338,817, filed on May 5, 2022, entitled "Systems and Methods for Monitoring and Controlling an Implantable Pulse Generator"; U.S. Provisional Application No. 63/339,024, filed on May 6, 2022, entitled "Programming and Calibration of Closed-Loop Vagal Nerve Stimulation Device"; U.S. Provisional Application No. 63/339,304, filed on May 6, 2022, entitled "Systems and Methods for Stimulating or Blocking a Nerve Using an Electrode Device with a Sutureless Closure"; U.S. Provisional Application No. 63/339,154, filed on May 6, 2022, entitled "Personalized Machine Learning Algorithm for Stimulation/Block Therapy for Treatment of Type 2 Diabetes"; U.S. Provisional Application No. 63/342,967, filed on May 17, 2022, entitled "Patient User Interface for a Stimulation/Block Therapy for Treatment of Type 2 Diabetes"; and U.S. Provisional Application No. 63/339,160, filed on May 6, 2022, entitled "Utilization of Growth Curves for Optimization of Type 2 Diabetes Treatment", all of which applications are incorporated herein by reference in their entireties.

BACKGROUND

The present disclosure is generally directed to therapeutic neuromodulation and relates more particularly to a stimulation/block therapy to affect insulin production of a patient.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic.

Additionally or alternatively, congenital hyperinsulinism, and more generally hyperinsulinism, is a condition where neonates or patients experience severe hypoglycemia (e.g., reduced blood sugar) due to abnormally high levels of insulin production that sometimes starts within the first few hours of birth. In some cases, the high levels of insulin production are due to a genetic mutation in potassium channels of the neonate/patient. Left untreated, congenital hyperinsulinism can be fatal.

BRIEF SUMMARY

Example aspects of the present disclosure include:

A system for stimulating an anatomical element of a patient, comprising: an implantable pulse generator configured to generate a current; an electrode device electrically coupled to the implantable pulse generator, the electrode device comprising a plurality of electrodes configured for placement on or around the anatomical element of the patient; a processor; and a memory storing data for processing by the processor, the data, when processed, causes the processor to: transmit instructions to the implantable pulse generator to apply the current generated to the anatomical element of the patient via the plurality of electrodes of the electrode device, wherein the current regulates insulin production of the patient.

Any of the aspects herein, wherein the anatomical element comprises a celiac vagal trunk and a hepatic vagal trunk of the patient.

Any of the aspects herein, further comprising: a first electrode of the plurality of electrodes configured for placement on or around the celiac vagal trunk; and a second electrode of the plurality of electrodes configured for placement on or around the hepatic vagal trunk.

Any of the aspects herein, wherein the data stored in the memory that, when processed causes the processor to transmit instructions to the implantable pulse generator to apply the current to the anatomical element further causes the system to: transmit instructions to the implantable pulse generator to apply the current to the celiac vagal trunk via the first electrode to downregulate neural activity of the celiac vagal trunk; and transmit instructions to the implantable pulse generator to apply the current to the hepatic vagal trunk via the second electrode to upregulate neural activity of the hepatic vagal trunk.

Any of the aspects herein, further comprising: a monitoring device configured to continuously monitor glucose levels in the patient, wherein the current is applied to the anatomical element based at least in part on the monitoring device detecting decreased glucose levels in the patient.

Any of the aspects herein, wherein insulin production of the patient is reduced based at least in part on the current being applied to the anatomical element.

Any of the aspects herein, wherein the insulin production of the patient is reduced at a pancreas of the patient.

Any of the aspects herein, wherein the current applied to anatomical element of the patient results in an increase in blood sugar levels of the patient.

A system for stimulating an anatomical element of a patient, comprising: an implantable pulse generator configured to generate a current; an electrode device comprising: a body; and a plurality of electrodes disposed on the body and configured to apply the current to the anatomical element; a processor; and a memory storing data for processing by the processor, the data, when processed, causes the processor to: transmit instructions to the implantable pulse generator to apply the current generated to the anatomical element of the patient via the plurality of electrodes of the electrode device, wherein the current regulates insulin production of the patient.

Any of the aspects herein, wherein the anatomical element comprises a celiac vagal trunk and a hepatic vagal trunk of the patient.

Any of the aspects herein, further comprising: a first electrode of the plurality of electrodes configured for placement on or around the celiac vagal trunk; and a second electrode of the plurality of electrodes configured for placement on or around the hepatic vagal trunk.

Any of the aspects herein, wherein the data stored in the memory that, when processed causes the processor to transmit instructions to the implantable pulse generator to apply the current to the anatomical element further causes the system to: transmit instructions to the implantable pulse generator to apply the current to the celiac vagal trunk via the first electrode to downregulate neural activity of the celiac vagal trunk; and transmit instructions to the implantable pulse generator to apply the current to the hepatic vagal trunk via the second electrode to upregulate neural activity of the hepatic vagal trunk.

Any of the aspects herein, further comprising: a monitoring device configured to continuously monitor glucose levels in the patient, wherein the current is applied to the anatomical element based at least in part on the monitoring device detecting decreased glucose levels in the patient.

Any of the aspects herein, wherein insulin production of the patient is reduced based at least in part on the current being applied to the anatomical element.

Any of the aspects herein, wherein the insulin production of the patient is reduced at a pancreas of the patient.

Any of the aspects herein, wherein the current applied to anatomical element of the patient results in an increase in blood sugar levels of the patient.

A system for regulating insulin production in a patient, comprising: an implantable pulse generator configured to generate a current; an electrode device electrically coupled to the implantable pulse generator, the electrode device comprising a plurality of electrodes; a first electrode of the plurality of electrodes configured for placement on or around a celiac vagal trunk of the patient, wherein the current generated by the implantable pulse generator is applied to the celiac vagal trunk via the first electrode; and a second electrode of the plurality of electrodes configured for placement on or around a hepatic vagal trunk of the patient, wherein the current generated by the implantable pulse generator is applied to the hepatic vagal trunk via the second electrode, and wherein the current regulates insulin production of the patient based at least in part on the current being applied to the celiac vagal trunk and the hepatic vagal trunk.

Any of the aspects herein, wherein: the current being applied to the celiac vagal trunk via the first electrode downregulates neural activity of the celiac vagal trunk; and the current being applied to the hepatic vagal trunk via the second electrode upregulates neural activity of the hepatic vagal trunk.

Any of the aspects herein, further comprising: a monitoring device configured to continuously monitor glucose levels in the patient, wherein the current is applied to the hepatic vagal trunk and the celiac vagal trunk based at least in part on the monitoring device detecting decreased glucose levels in the patient.

Any of the aspects herein, wherein insulin production of the patient is reduced based at least in part on the current being applied to the hepatic vagal trunk and the celiac vagal trunk.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
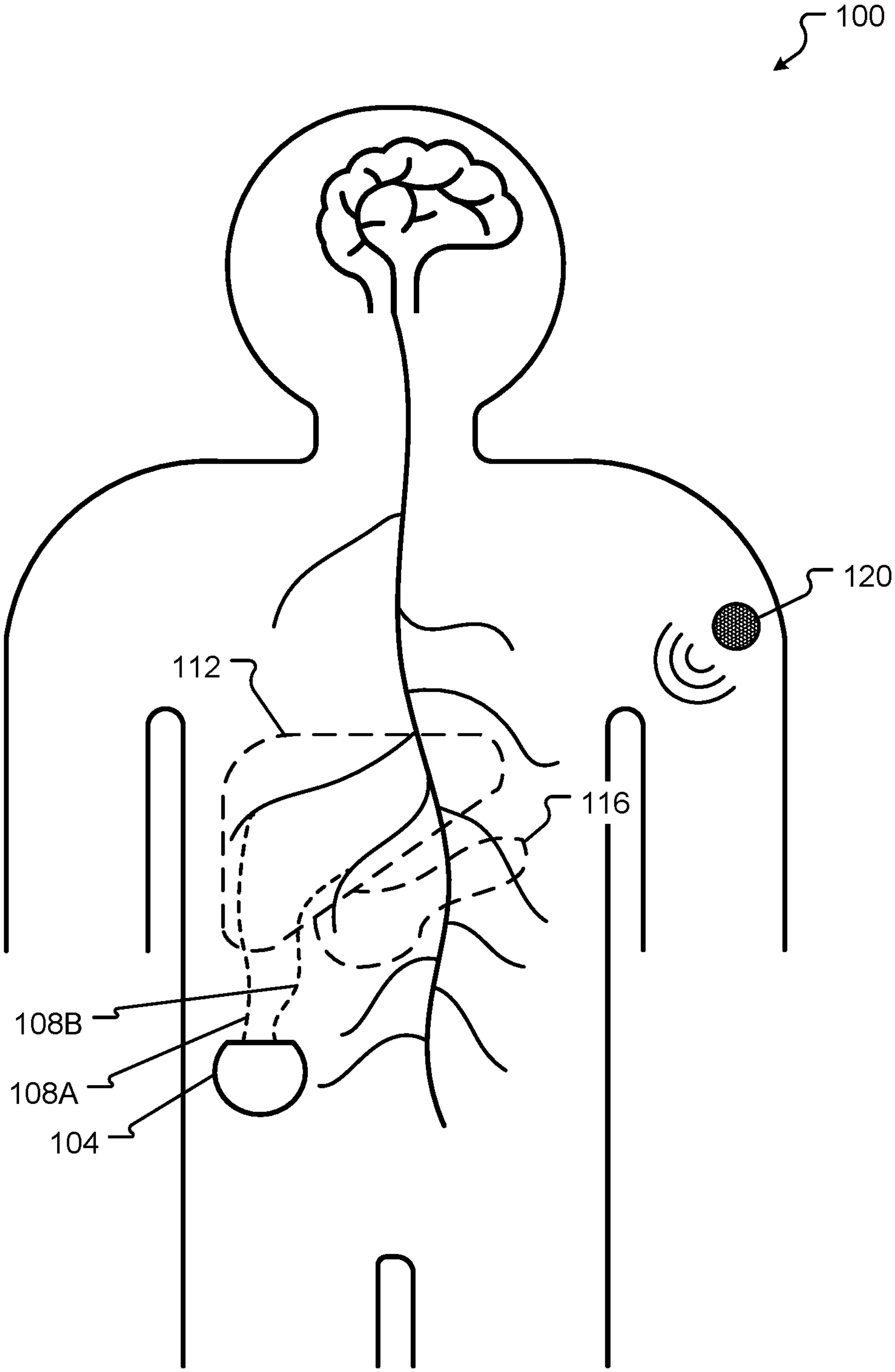
FIG. 1 is a diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., random-access memory (RAM), read-only memory (ROM), electrically erasable programmable ROM (EEPROM), flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. The processors listed herein are not intended to be an exhaustive list of all possible processors that can be used for implementation of the described techniques, and any future iterations of such chips, technologies, or processors may be used to implement the techniques and embodiments of the present disclosure as described herein.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Vagus nerve stimulation (VNS) is a technology that has been developed to treat different disorders or ailments of a patient, such as epilepsy and depression. In some examples, VNS involves placing a device in or on a patient's body that uses electrical impulses to stimulate the vagus nerve. For example, the device may be usually placed under the skin of the patient, where a wire (e.g., lead) and/or electrode connects the device to the vagus nerve. Once the device is activated, the device sends signals through the vagus nerve to the patient's brainstem (e.g., or different target area in the patient, such as other organs of the patient), transmitting information to their brain. For example, with VNS, the device may be configured to send regular, mild pulses of electrical energy to the brain via the vagus nerve. In some examples, the device may be referred to as an implantable pulse generator. An implantable vagus nerve stimulator has been approved to treat epilepsy and depression in qualifying patients.

The vagus nerve (e.g., also called the pneumogastric nerve, vagal nerve, the cranial nerve X, etc.) is responsible for various internal organ functions of a patient, including digestion, heart rate, breathing, cardiovascular activity, and reflex actions (e.g., coughing, sneezing, swallowing, and vomiting). Most patients may have one vagus nerve on each side of their body, with numerous branches running from their brainstem through their neck, chest, and abdomen down to part of their colon. The vagus nerve plays a role in many bodily functions and may form a link between different areas of the patient, such as the brain and the gut. The vagus nerve is a critical nerve for supplying parasympathetic information to the visceral organs of the respiratory, digestive, and urinary systems. Additionally, the vagus nerve is important in the control of heart rate, bronchoconstriction, and digestive processes. In some cases, the vagus nerve may be considered a mixed nerve based on including both afferent (sensory) fibers and efferent (motor) fibers. As such, based on including the two types of fibers, the vagus nerve may be responsible for carrying motor signals to organs for innervating the organs (e.g., via the efferent fibers), as well as carrying sensory information from the organs back to the brain (e.g., via the afferent fibers).

The vagus nerve has a number of different functions. Four key functions of the vagus nerve are carrying sensory signals, carrying special sensory signals, providing motor functions, and assisting in parasympathetic functions. For example, the sensory signals carried by the vagus nerve may include signaling between the brain and the throat, heart, lungs, and abdomen. The special sensory signals carried by the vagus nerve may provide signaling of special senses in the patient, such as the taste sensation behind the tongue. Additionally, the vagus nerve may enable certain motor functions of the patient, such as providing movement functions for muscles in the neck responsible for swallowing and speech. The parasympathetic functions provided by the vagus nerve may include digestive tract, respiration, and heart rate functioning. In some cases, the nervous system can be divided into two areas: sympathetic and parasympathetic. The sympathetic side increases alertness, energy, blood pressure, heart rate, and breathing rate. The parasympathetic side, which the vagus nerve is heavily involved in, decreases alertness, blood pressure, and heart rate, and helps with calmness, relaxation, and digestion.

VNS is considered a type of neuromodulation (e.g., a technology that acts directly upon nerves of a patient, such as the alteration, or "modulation," of nerve activity by delivering electrical impulses or pharmaceutical agents directly to a target area). For example, as described above, VNS may include using a device (e.g., implanted in a patient or attached to the patient) that is configured to send regular, mild pulses of electrical energy to a target area of the patient (e.g., brainstem, organ, etc.) via the vagus nerve. The electrical pulses or impulses may affect how that target area of the patient functions to potentially treat different disorders or ailments of a patient.

In some examples, for epileptic patients that suffer from seizures, VNS may change how brain cells work by applying electrical stimulation to certain areas involved in seizures. For example, research has shown that VNS may help control seizures by increasing blood flow in key areas, raising levels of some brain substances (e.g., neurotransmitters) important to control seizures, changing electroencephalogram (EEG) patterns during a seizure, etc. As an example, an epileptic patient's heart rate may increase during a seizure or epileptic episode, so the VNS device may be programmed to send stimulation to the vagus nerve regular intervals and when periods of increased heart rate are seen, where applying stimulation at those times of increased heart rate may help stop seizures. Additionally or alternatively, depression has been tied to an imbalance in certain brain chemicals (e.g., neurotransmitters), so VNS is believed to assist in treating patients diagnosed with depression by using electricity (e.g., electrical pulses/impulses) to influence the production of those brain chemicals.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic. Additionally, in a financial sense, global expenditures for type 2 diabetes treatments, preventive measures, and resulting consequences are estimated at about $966 billion per year. Compounding this issue of high global expenditures is the increasing price of insulin.

As described herein, a neuromodulation technique is provided for glycemic control (e.g., as a treatment for diabetes) using a stimulation/block therapy (e.g., type of VNS). For example, the neuromodulation technique may generally include using a device (e.g., including at least an implantable pulse generator) to provide electrical stimulation (e.g., electrical pulses/impulses) on one or more trunks of the vagus nerve (e.g., vagal trunks) to mute a glycemic response for patients with diabetes. The "patient" as used herein may refer to *Homo sapiens* or any other living being that has a vagus nerve.

In some examples, the device may provide stimulation/blocking of the celiac and hepatic vagal trunks (e.g., using the device) for the purposes of glycemic control. For example, the anterior sub diaphragmatic vagal trunk at the hepatic branching point of the vagus nerve may be electrically blocked (e.g., down-regulated) by delivering a high frequency stimulation (e.g., of about 5 kilohertz (kHz) or in a range between 1 kHz to 50 kHz). Additionally or alternatively, the posterior sub diaphragmatic vagal trunk at the celiac branching point of the vagus nerve may be electrically stimulated (e.g., up-regulated) by delivering a low frequency stimulation (e.g., a square wave at 1 Hz or within a range from 0.1 to 20 Hz). In some examples, the electrical blocking and/or electrical stimulating of the respective vagal trunks may be performed by using one or more cuff electrodes (e.g., of the device) placed on the corresponding vagal trunks (e.g., sutured or otherwise held in place). The desired response by providing the stimulation/block therapy is a muting of the glycemic response of a patient. In some examples, muting of the glycemic response may refer to a lower post prandial peak of the glycemic response as compared to a peak without the stimulation/block therapy being applied.

Using the stimulation/block therapy to achieve a muting of the glycemic response is advantageous for those with type 2 diabetes where the postprandial glycemic response (e.g., occurring after a meal) can be very high. For example, some patients with type 2 diabetes may have high blood sugar levels (e.g., glucose levels) after eating a meal based on their reduced or lack of insulin production (e.g., normal insulin production in the body lowers blood sugar levels postprandially by promoting absorption of glucose from the blood into different cells). Additionally or alternatively, patients diagnosed with type 2 diabetes may generally have high glycemic levels at different points of the day (e.g., not necessarily postprandially or immediately after a meal). Over time, the effect of high glycemic values can have a detrimental effect on one's health, leading to neuropathy, retinopathy, and other ailments. Accordingly, by using the stimulation/block therapy provided herein, a high glycemic response experienced by type 2 diabetes patients may be muted (e.g., the glycemic response is reduced, particularly post prandially). Additionally, the therapy aims to improve insulin sensitivity by blocking hepatic glucose production and also by stimulating pancreatic insulin production needed for glycemic control, where the lack of insulin sensitivity can potentially lead to an imbalance in glycemic control and consequent systemic complications in patients with type 2 diabetes. In some examples, the therapy may also improve fasting hyperglycemia, which can be commonly seen in patients with type 2 diabetes.

Additionally or alternatively, as described herein, a device (e.g., implantable pulse generator) configured to provide a stimulation to the celiac and hepatic vagal trunks (e.g., or another anatomical element of the patient) may be used in the context of treating hyperinsulinism (e.g., congenital hyperinsulinism). Congenital hyperinsulinism, and more generally hyperinsulinism, is a condition where neonates or patients experience severe hypoglycemia (e.g., reduced blood sugar) due to abnormally high levels of insulin production that sometimes starts within the first few hours of birth. In some cases, the high levels of insulin production are due to a genetic mutation in potassium channels of the neonate/patient (e.g., adenosine triphosphate (ATP)-sensitive potassium (kATP or $K_{ATP}$) channels). Left untreated, congenital hyperinsulinism can be fatal. In many cases, children diagnosed with hyperinsulinism or congenital hyperinsulinism do not survive very long.

In some cases, the only treatment currently available for treating hyperinsulinism and congenital hyperinsulinism is a pancreatectomy (e.g., removal of a patient's pancreas). However, pancreatectomies come with different problems. Due to having their pancreas removed, the patients may be unable to digest food on their own and may rely on other feeding methods to properly digest their meals. Further, with no pancreas, the patient's body may be unable to regulate its own blood glucose, such that the patients require around-the-clock glucose management through insulin and glucagon injections or pump therapy, affecting the patient's lifestyle drastically from an early age (e.g., sometimes all before the patient is two (2) years of age).

Hyperinsulinism is the most frequent cause of severe, persistent hypoglycemia in newborn babies, infants, and children. In most countries, hyperinsulinism occurs in approximately 1/25,000 to 1/50,000 births. About 60% of babies with hyperinsulinism are diagnosed during the first month of life. An additional 30% of babies with hyperinsulinism are diagnosed after the first month but within their first year of life, and the remainder of patients with hyperinsulinism are diagnosed after that first year of life.

Using techniques described herein, neuromodulation techniques are provided that can be used to treat hyperinsulinism and/or other metabolic syndromes. For example, the neuromodulation techniques may include delivering a current or signal to one or more branches of the vagus nerve that results in a blocking of the celiac branch of a patient's vagus nerve (e.g., celiac vagal trunk) that regulates insulin production from the patient's pancreas. Blocking the celiac branch of the vagus nerve may offer patients a better chance of managing hyperinsulinism.

As part of blocking the celiac branch of the vagus nerve, electrodes (e.g., one or more cuff electrodes) may be placed on the celiac branch of the vagus nerve and/or other branches of the vagus nerve, and the electrodes may be configured to deliver a current or signal (e.g., generated by an implantable pulse generator) to the branch(es) of the vagus nerve, such that the current or signal blocks neural activity on the celiac branch of the vagus nerve that regulates insulin production in the patient. For example, the current may be used to deliver a high frequency stimulation to the celiac branch of the vagus nerve that blocks neural activity of the celiac branch, which then blocks signaling to the pancreas that would otherwise cause the pancreas to produce excessive amounts of insulin in the patient. Accordingly, medical professionals (e.g., pediatricians) and the patients may be able to block excess insulin production and regulate insulin production at will for the patient using the stimulation therapy and neuromodulation techniques described herein.

Further, because the stimulation therapy obviates the need for a pancreatectomy, patients do not have to rely on alternative feeding methods (e.g., such as consuming partially digested food). Thus, the nerve modulation therapy may offer patients both a chance at a longer and healthier life and a better lifestyle. In some examples, the patients may use continuous glucose monitoring (e.g., via a glucose sensor) while on the nerve modulation therapy to achieve better glycemic control.

Embodiments of the present disclosure provide technical solutions to one or more of the problems of (1) treating congenital hyperinsulinism and, more generally, hyperinsulinism and (2) lifestyle impacts that result from pancreatectomies. For example, the nerve modulation therapy provided herein can be used to treat hyperinsulinism and congenital hyperinsulinism by providing electrical stimulation to one or more vagal trunks of a patient to regulate or decrease insulin production in the patient. Additionally, the nerve modulation therapy obviates the need for a pancreatectomy, thereby increasing a standard of living for the patient that would have otherwise been impacted by the removal of a patient's pancreas, such as requiring the patient to consume partially digested food or around-the-clock glucose management through insulin and glucagon injections or pump therapy.

Turning to FIG. 1, a diagram of a system 100 according to at least one embodiment of the present disclosure is shown. The system 100 may be used to provide insulin production regulation for a patient and/or carry out one or more other aspects of one or more of the methods disclosed herein. For example, the system 100 may include at least a device 104 that is capable of providing a stimulation/blocking therapy that blocks excessive insulin production for patients with hyperinsulinism. In some examples, the device 104 may be referred to as an implantable pulse generator. Additionally, the system 100 may include one or more wires 108 (e.g., leads) that provide a connection between the device 104 and nerves of the patient for enabling the stimulation/blocking therapy.

As described previously, neuromodulation techniques (e.g., technologies that act directly upon nerves of a patient, such as the alteration, or "modulation," of nerve activity by delivering electrical impulses or localized pharmaceutical agents directly to a target area) may be used for assisting in treatments for different diseases, disorders, or ailments of a patient, such as epilepsy and depression. Accordingly, as described herein, the neuromodulation techniques may be used for blocking excess insulin production in the patient to assist in the treatment of hyperinsulinism for the patient. For example, the device 104 may provide electrical stimulation to one or more trunks of the vagus nerve of the patient (e.g., via the one or more wires 108) to provide the stimulation/blocking therapy for supporting insulin regulation in the patient.

In some examples, the one or more wires 108 may include at least a first wire 108A and a second wire 108B connected to respective vagal trunks (e.g., different trunks of the vagus nerve). As described previously, most patients have one vagus nerve on each side of their body, with numerous branches or trunks running from their brainstem through their neck, chest, and abdomen down to part of their colon. The vagus nerve plays a role in many bodily functions and may form a link between different areas of the patient, such as the brain and the gut. For example, the vagus nerve is responsible for various internal organ functions of a patient, including digestion, heart rate, breathing, cardiovascular activity, and reflex actions (e.g., coughing, sneezing, swallowing, and vomiting).

Accordingly, the first wire 108A may be connected to a first vagal trunk of the patient (e.g., the posterior sub diaphragmatic vagal trunk at the celiac branching point of the vagus nerve, celiac vagal trunk, celiac branch of the vagus nerve, etc.) to provide an electrical blocking signal (e.g., a down-regulating signal) from the device 104 to the first vagal trunk (e.g., by delivering a high frequency stimulation, such as a given waveform at about 5 kHz or within a range from 1 kHz to 50 kHz). Additionally or alternatively, the second wire 108B may be connected to a second vagal trunk of the patient (e.g., the anterior sub diaphragmatic vagal trunk at the hepatic branching point of the vagus nerve, hepatic vagal trunk, hepatic branch of the vagus nerve, etc.) to provide an electrical stimulation signal (e.g., an up-regulating signal) from the device 104 to the second vagal trunk (e.g., by delivering a low frequency stimulation, such as a square wave or other waveform at 1 Hz or within a range from 0.1 to 20 Hz). By providing the electrical blocking signal and the electrical stimulation signal to the respective vagal trunks, the system 100 may provide a blocking of excessive insulin production in the patient when the stimulation/blocking therapy is applied.

In some examples, the vagal trunks to which the wires 108 are connected may be connected to or otherwise in the vicinity of one or more organs of the patient, such that the blocking/stimulation signals provided to the respective vagal trunks by the wires 108 and the device 104 are delivered to the one or more organs. For example, the first vagal trunk (e.g., to which the first wire 108A is connected) may be connected to a first organ 112 of the patient, and the second vagal trunk (e.g., to which the second wire 108B is connected) may be connected to a second organ 116. Additionally or alternatively, while the respective vagal trunks are shown as being connected to the corresponding organs of the patient as described, the vagal trunks to which the wires 108 are connected may be connected to the other organ (e.g., the first vagal trunk is connected to the second organ 116 and the second vagal trunk is connected to the first organ 112) or may be connected to different organs of the patient. In some examples, the first organ 112 may represent a liver of the patient, and the second organ 116 may represent a pancreas of the patient. In such examples, the blocking/stimulation signals provided by the wires 108 and the device 104 may be delivered to the liver and/or pancreas of the patient to block excessive insulin production in the patient as described herein.

In some examples, the wires 108 may provide the electrical signals to the respective vagal trunks via electrodes of an electrode device (e.g., cuff electrodes) that are connected to the vagal trunks (e.g., sutured in place, wrapped around the nerves of the vagal trunks, etc.). In some examples, the wires 108 may be referenced as cuff electrodes or may otherwise include the cuff electrodes (e.g., at an end of the wires 108 not connected or plugged into the device 104). Additionally or alternatively, while shown as physical wires that provide the connection between the device 104 and the one or more vagal trunks, the cuff electrodes may provide the electrical blocking and/or stimulation signals to the one or more vagal trunks wirelessly (e.g., with or without the device 104).

Additionally, while not shown, the system 100 may include one or more processors (e.g., one or more DSPs, general purpose microprocessors, graphics processing units, ASICs, FPGAs, or other equivalent integrated or discrete logic circuitry) that are programmed to carry out one or more aspects of the present disclosure. In some examples, the one or more processors may include a memory or may be otherwise configured to perform the aspects of the present disclosure. For example, the one or more processors may provide instructions to the device 104, the cuff electrodes, or other components of the system 100 not explicitly shown or described with reference to FIG. 1 for providing the stimulation/blocking therapy to regulate insulin production in a patient as described herein. In some examples, the one or more processors may be part of the device 104 or part of a control unit for the system 100 (e.g., where the control unit is in communication with the device 104 and/or other components of the system 100).

In some examples, the system 100 may also optionally include a glucose sensor 120 that communicates (e.g., wirelessly) with other components of the system 100 (e.g., the device 104, the one or more processors, etc.) to achieve better glycemic control in addition to regulating insulin production. For example, the glucose sensor 120 may continuously monitor glucose levels of the patient, such that if the glucose sensor 120 determines glucose levels are low in the patient (e.g., or outside a normal or desired range for the patient, such that glucose levels are determined to be too high or too low in the patient), the glucose sensor 120 may communicate that glucose levels are getting low to the device 104 (e.g., via the one or more processors) to signal for the device 104 to apply the stimulation/blocking therapy described herein to block insulin production in the patient as a possible technique to raise glucose levels in the patient.

The system 100 or similar systems may be used, for example, to carry out one or more aspects of any of the methods 300 and/or 400 described herein. The system 100 or similar systems may also be used for other purposes. It will be appreciated that the human body has many vagal nerves and the stimulation and/or blocking therapies described herein may be applied to one or more vagal nerves, which may reside at any location of a patient (e.g., lumbar, thoracic, etc.). Further, a sequence of stimulations and/or blocking therapies may be applied to different nerves. For example, a low frequency stimulation may be applied to a first nerve and a high frequency blockade may be applied to a second nerve.

Figure 2:
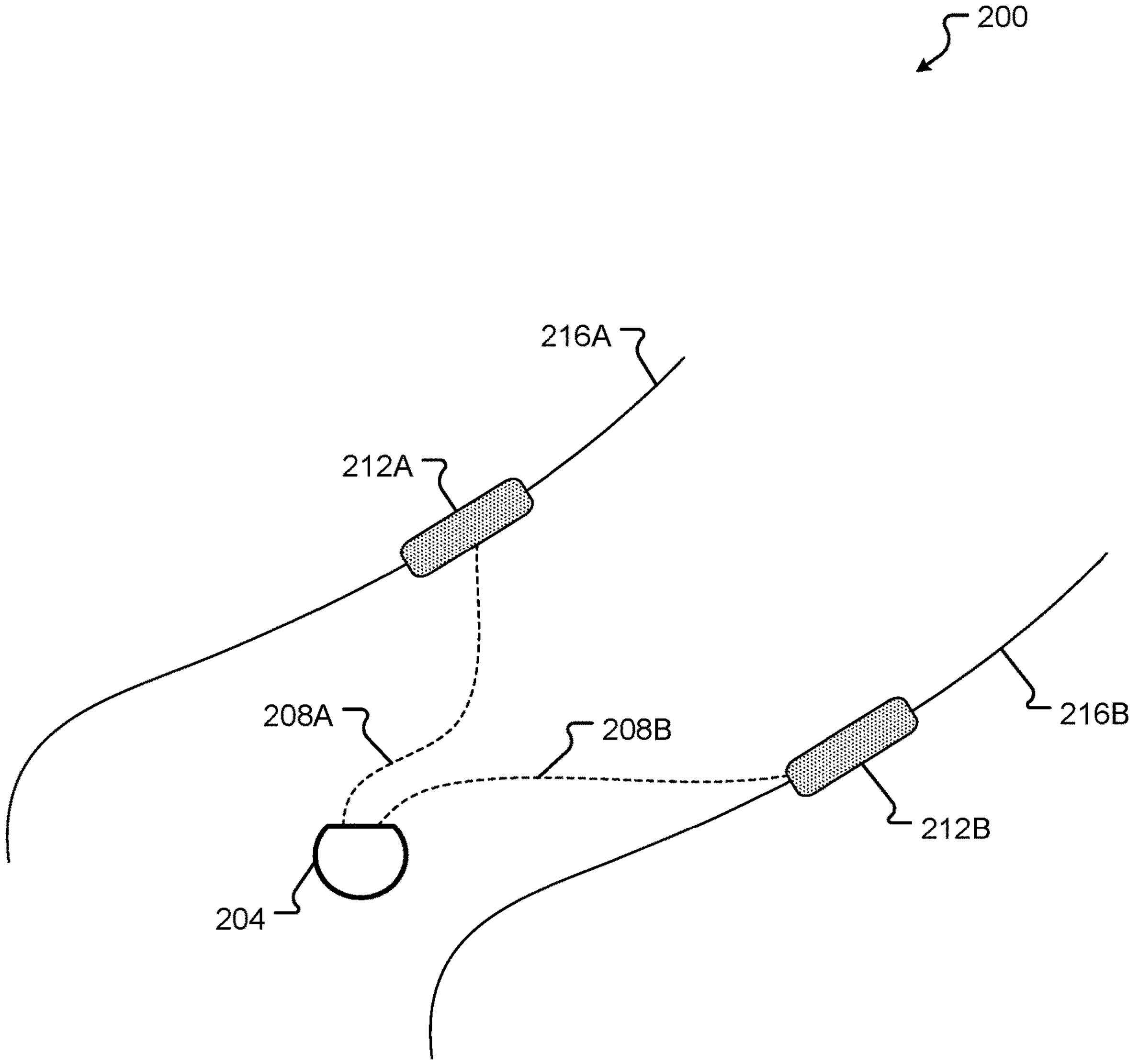
FIG. 2 is a diagram of an additional system according to at least one embodiment of the present disclosure.

FIG. 2 depicts a system 200 according to at least one embodiment of the present disclosure is shown. In some examples, the system 200 may implement aspects of or may be implemented by aspects of the system 100 as described with reference to FIG. 1. For example, the system 200 may be used to provide insulin production regulation for a patient and/or carry out one or more other aspects of one or more of the methods disclosed herein. Additionally, the system 200 may include at least a device 204 that is capable of providing a stimulation/blocking therapy that blocks excessive insulin production for patients with hyperinsulinism. In some examples, the device 204 may be referred to as an implantable pulse generator or implantable neurostimulator. Additionally, the system 200 may include one or more wires 208 (e.g., leads) that provide a connection between the device 204 and nerves of the patient for enabling the stimulation/blocking therapy. The device 204 and the one or more wires 208 may represent examples of the corresponding device 104 and the one or more wires 108, respectively, as described with reference to FIG. 1.

The system 200 may block excess insulin production in the patient by delivering a current generated by the device 204 to an anatomical element via the one or more wires 208. For example, the current may be applied to one or more vagal trunks 216 of the patient using one or more electrode devices 212 that receive the current from the device 204 (e.g., via the wires 208 or wirelessly). In some examples, the electrode devices 212 may each include a body and a plurality of electrodes that are disposed on the respective bodies, where the plurality of electrodes are configured to apply the current generated by the device 204 to the one or more vagal trunks 216. As shown, a first electrode device 212A (e.g., a first electrode or first cuff electrode) may be configured for placement on a first vagal trunk 216A to apply a current to the first vagal trunk 216A (e.g., carried via a first wire 208A or wirelessly instructed to apply the current), and a second electrode device 212B (e.g., a second electrode or second cuff electrode) may be configured for placement on a second vagal trunk 216B to apply a current to the second vagal trunk (e.g., carried via a second wire 208B or wirelessly instructed to apply the current). In some examples, the electrode devices 212 may be referred to as cuff electrodes.

In some examples, the first vagal trunk 216A may represent a celiac vagal trunk of the patient, and the second vagal trunk 216B may represent a hepatic vagal trunk of the patient. Accordingly, applying the current to the first vagal trunk 216A via the first electrode device 212A may downregulate (e.g., block) neural activity of the celiac vagal trunk, and applying the current to the second vagal trunk 216B via the second electrode device 212B may upregulate (e.g., stimulate) neural activity of the hepatic vagal trunk. By downregulating the neural activity of the celiac vagal trunk, excess insulin production in the patient may be blocked or reduced based on signaling between the celiac vagal trunk and a patient's pancreas being blocked, resulting in the pancreas decreasing insulin production and aiding in the treatment of hyperinsulinism.

In some examples, the current being applied to each vagal trunk 216 may be different per electrode device 212 or may include different parameters for application to each vagal trunk. For example, the first electrode device 212A may apply a high frequency stimulation (e.g., such as a given waveform at about 5 kHz) to provide an electrical blocking signal (e.g., a down-regulating signal) from the device 204 to the first vagal trunk 216A. Additionally or alternatively, the second electrode device 212B may apply a low frequency stimulation (e.g., such as a square wave or other waveform at 1 Hz) to provide an electrical stimulation signal (e.g., an up-regulating signal) from the device 204 to the second vagal trunk 216B. The combined effect of providing the same current with different parameters or respective currents with respective parameters to each of the vagal trunks 216 may result in providing a blocking of excessive insulin production in the patient when the stimulation/blocking therapy is applied. Subsequently, the patient may also experience an increase in blood sugar or glucose levels based on applying the stimulation/blocking therapy (e.g., to mitigate hypoglycemia).

Additionally, while not shown, the system 200 may also include a monitoring device (e.g., a glucose sensor) that is configured to continuously monitor glucose levels in the patient. In some examples, the electrode devices 212 may apply the current(s) to the vagal trunks 216 based on the monitoring device detecting decreased glucose levels in the patient. Accordingly, the monitoring device may communicate (e.g., wirelessly) with other components of the system 200 (e.g., the device 204, one or more processors, etc.) to achieve better glycemic control in addition to regulating insulin production. For example, the monitoring device may determine glucose levels are low in the patient and, as such, may communicate that glucose levels are getting low to the device 204 (e.g., via the one or more processors or directly) to signal for the device 204 to apply the stimulation/blocking therapy described herein to block insulin production in the patient as a possible technique to raise glucose levels in the patient and mitigate hyperinsulinism and/or hypoglycemia in the patient.

Figure 3:
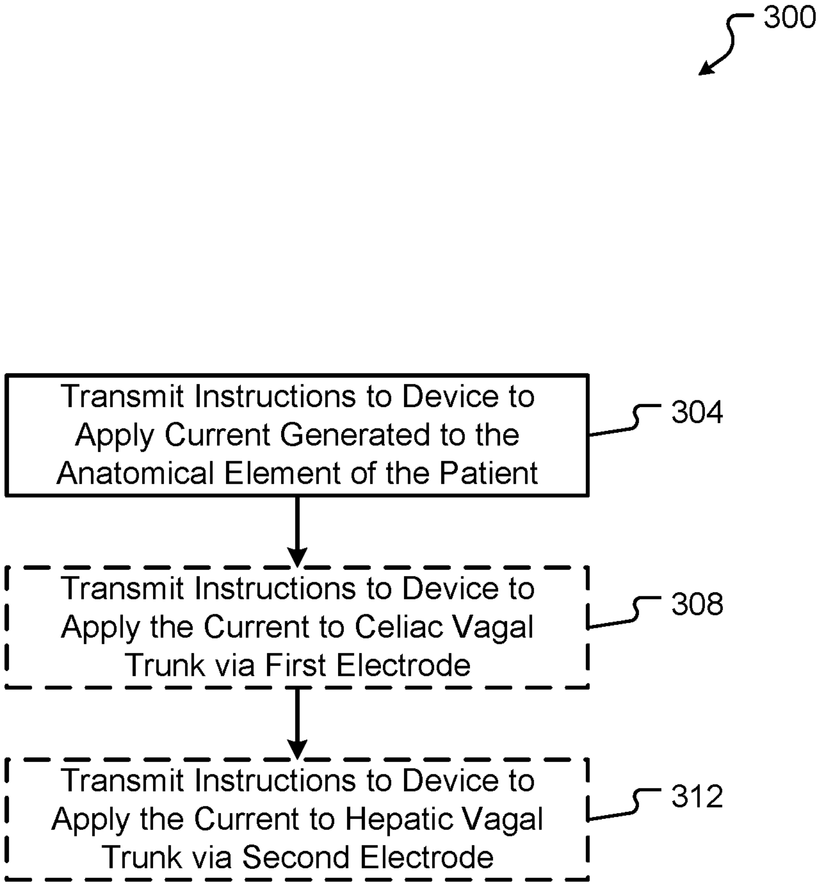
FIG. 3 is a flowchart according to at least one embodiment of the present disclosure.

FIG. 3 depicts a method 300 that may be used, for example, to perform neuromodulation techniques (e.g., a stimulation/block therapy) to provide insulin production regulation for a patient to treat hyperinsulinism in the patient.

The method 300 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 300. The at least one processor may perform the method 300 by executing elements stored in a memory (such as a memory in the device 104 as described above or a control unit). The elements stored in the memory and executed by the processor may cause the processor to execute one or more steps of a function as shown in method 300. One or more portions of a method 300 may be performed by the processor executing any of the contents of memory, such as providing a stimulation/block therapy and/or any associated operations as described herein.

The method 300 comprises transmitting instructions to a device (e.g., the device 104 or 204 as described with reference to FIGS. 1 and 2, such as an implantable pulse generator) to apply a current generated by the device to an anatomical element of the patient via a plurality of electrodes of an electrode device, where the current regulates insulin production of the patient (step 304). In some examples, the anatomical element may comprise a celiac vagal trunk and a hepatic vagal trunk of the patient. Accordingly, a first electrode of the plurality of electrodes may be configured for placement on the celiac vagal trunk, and a second electrode of the plurality of electrodes may be configured for placement on the hepatic vagal trunk.

The method 300 also comprises transmitting instructions to the device to apply the current to the celiac vagal trunk via the first electrode to downregulate neural activity of the celiac vagal trunk (step 308). The method 300 also comprises transmitting instructions to the device to apply the current to the hepatic vagal trunk via the second electrode to upregulate neural activity of the hepatic vagal trunk (step 312). By applying the current to the respective vagal trunks to downregulate/upregulate the corresponding neural activity of each vagal trunk, the patient may be able to regulate their insulin production at will. For example, insulin production of the patient may be reduced based on applying the current to the vagal trunks (e.g., insulin production of the patient is reduced at a pancreas of the patient). Additionally, applying the current to the vagal trunks may result in an increase in blood sugar or glucose levels in the patient.

The present disclosure encompasses embodiments of the method 300 that comprise more or fewer steps than those described above, and/or one or more steps that are different than the steps described above.

Figure 4:
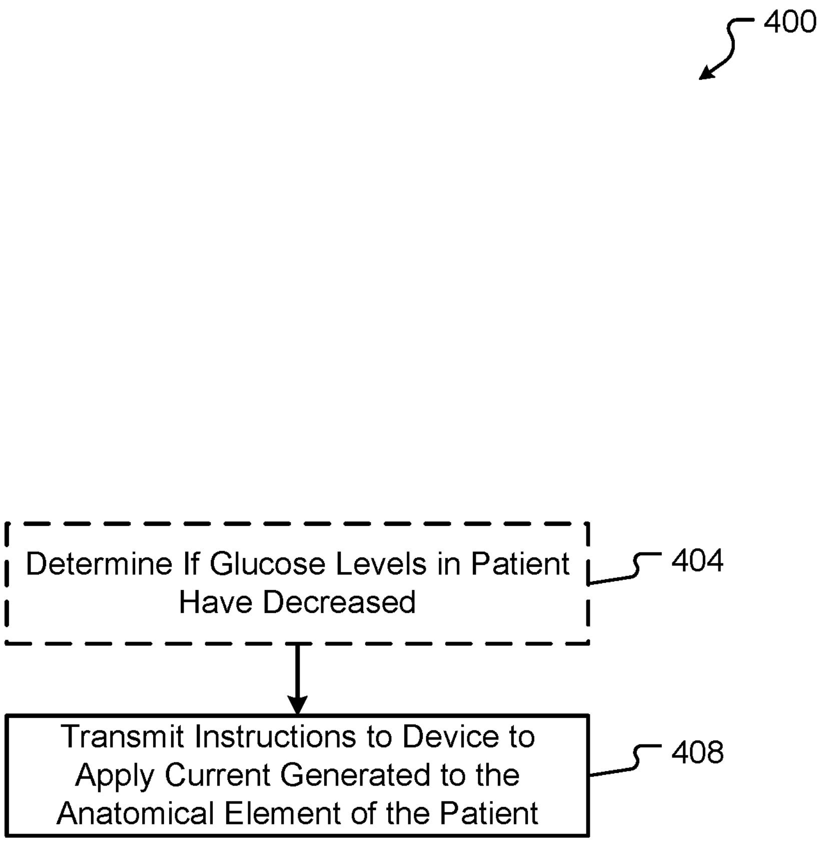
FIG. 4 is a flowchart according to at least one embodiment of the present disclosure.

FIG. 4 depicts a method 400 that may be used, for example, to provide better glycemic control for a patient in addition to providing a stimulation therapy to regulate insulin production in the patient.

The method 400 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 400. The at least one processor may perform the method 400 by executing elements stored in a memory (such as a memory in the device 104 as described above or a control unit). The elements stored in the memory and executed by the processor may cause the processor to execute one or more steps of a function as shown in method 400. One or more portions of a method 400 may be performed by the processor executing any of the contents of memory, such as providing a stimulation/block therapy and/or any associated operations as described herein.

The method 400 comprises determining if glucose levels in a patient have decreased (step 404). For example, the patient may have a monitoring device attached to themselves or implanted within themselves (e.g., the glucose sensor 112 as described with reference to FIG. 1) that is configured to continuously monitor glucose levels in the patient. Accordingly, this monitoring device may communicate with the at least one processor to indicate if glucose levels in the patient are low or fall below a threshold value. In some examples, low glucose levels may be representative of hyperinsulinism and/or hypoglycemia. As such, if the glucose levels become low, the neuromodulation techniques for applying the stimulation/block therapy as described herein may be used to decrease insulin production and/or increase glucose levels in the patient.

The method 400 also comprises transmitting instructions to a device (e.g., the device 104 or 204 as described with reference to FIGS. 1 and 2, such as an implantable pulse generator) to apply the current generated by the device to the anatomical element of the patient via the plurality of electrodes of the electrode device (step 408). In some examples, the processor may determine to transmit the instructions to the device to apply the generated current to the anatomical element based on determining the glucose levels in the patient have decreased.

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that comprise one or more steps from one method described herein, and one or more steps from another method described herein. Any correlation described herein may be or comprise a registration or any other correlation.

Figure 5:
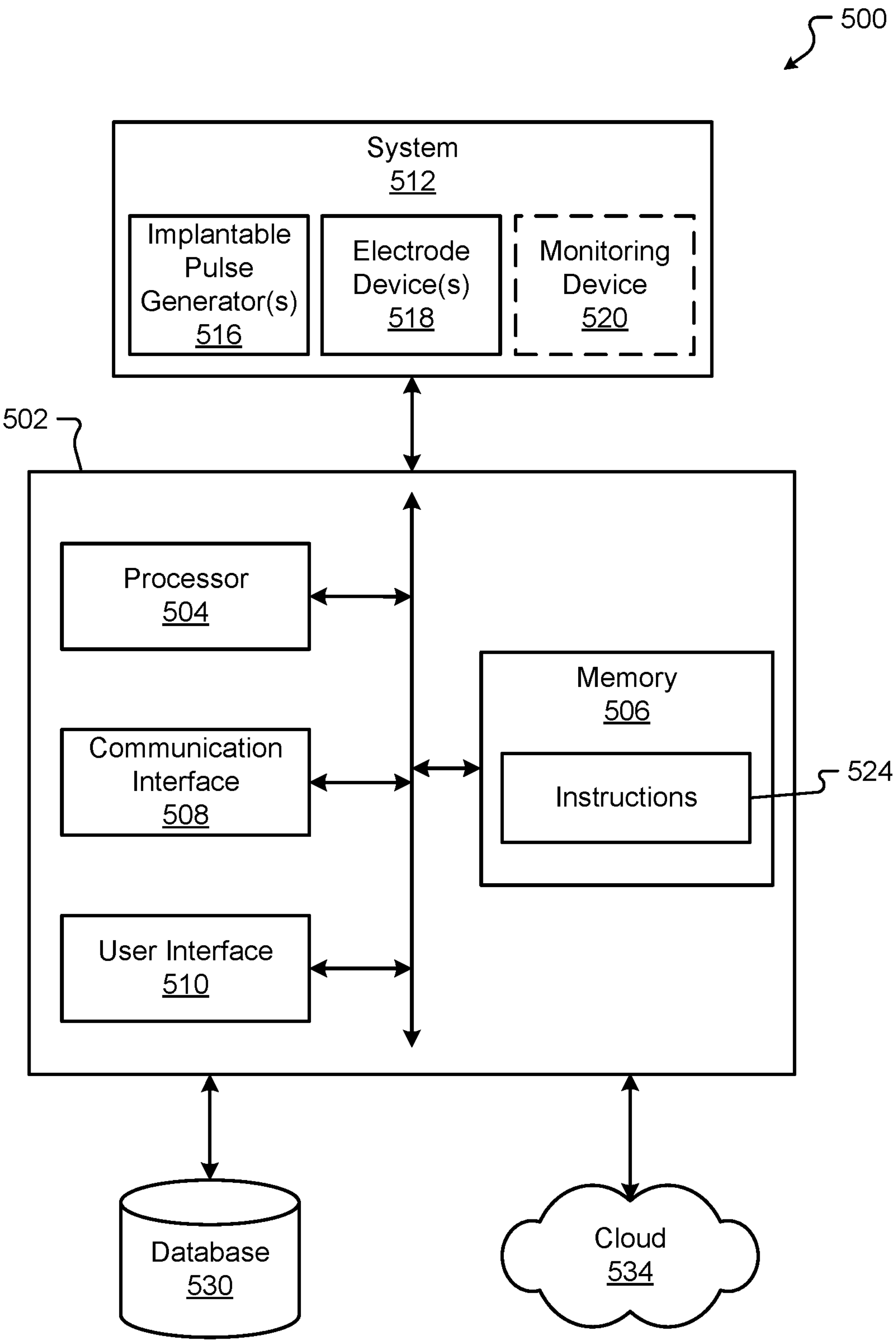
FIG. 5 is a block diagram of a system according to at least one embodiment of the present disclosure.

FIG. 5 depicts a block diagram of a system 500 according to at least one embodiment of the present disclosure is shown. In some examples, the system 500 may implement aspects of or may be implemented by aspects of FIGS. 1-4 as described herein. For example, the system 500 may be used with an implantable pulse generator 516 and/or an electrode device 518, and/or carry out one or more other aspects of one or more of the methods disclosed herein. The implantable pulse generator 516 may represent an example of the device 104, 204 or a component of the device 104, 204 as described with reference to FIGS. 1 and 2, where the electrode device 518 may represent the wires 108, 208 and corresponding electrodes/cuff electrodes as described with reference to FIGS. 1 and 2 (e.g., including the electrode devices 212). Additionally or alternatively, the system 500 may be used with a monitoring device 520 and/or may carry out one or more other aspects of one or more of the methods disclosed herein. The monitoring device 520 may represent an example of the glucose sensor 112 as described with reference to FIG. 1 or the monitoring device as described with reference to FIGS. 2 and 4. The system 500 comprises a computing device 502, a system 512, a database 530, and/or a cloud or other network 534. Systems according to other embodiments of the present disclosure may comprise more or fewer components than the system 500. For example, the system 500 may not include one or more components of the computing device 502, the database 530, and/or the cloud 534.

The system 512 may comprise the implantable pulse generator 516 and the electrode device 518. As previously described, the implantable pulse generator 516 may be configured to generate a current, and the electrode device 518 may comprise a plurality of electrodes configured to apply the current to an anatomical element. Additionally or alternatively, the system 512 may comprise the monitoring device 520 that is configured to continuously monitor glucose levels in the patient (e.g., such that the current is applied to the anatomical element based in part on the monitoring device 520 detecting decreased glucose levels in the patient). The system 512 may communicate with the computing device 502 to receive instructions such as instructions 524 for applying a current to the anatomical element, where the current is intended to regulate insulin production of the patient. The system 512 may also provide data (such as data received from an electrode device 518 capable of recording data), which may be used to optimize the electrodes of the electrode device 518 and/or to optimize parameters of the current generated by the implantable pulse generator 516.

The computing device 502 comprises a processor 504, a memory 506, a communication interface 508, and a user interface 510. Computing devices according to other embodiments of the present disclosure may comprise more or fewer components than the computing device 502.

The processor 504 of the computing device 502 may be any processor described herein or any similar processor. The processor 504 may be configured to execute instructions 524 stored in the memory 506, which instructions may cause the processor 504 to carry out one or more computing steps utilizing or based on data received from the system 512, the database 530, and/or the cloud 534.

The memory 506 may be or comprise RAM, DRAM, SDRAM, other solid-state memory, any memory described herein, or any other tangible, non-transitory memory for storing computer-readable data and/or instructions. The memory 506 may store information or data useful for completing, for example, any steps of the methods 300 and/or 400 described herein, or of any other methods. The memory 506 may store, for example, instructions and/or machine learning models that support one or more functions of the system 512. For instance, the memory 506 may store content (e.g., instructions 524 and/or machine learning models) that, when executed by the processor 504, cause the electrode device(s) 518 to apply a current to respective vagal trunks of the patient to regulate insulin production in the patient.

Content stored in the memory 506, if provided as in instruction, may, in some embodiments, be organized into one or more applications, modules, packages, layers, or engines. Alternatively or additionally, the memory 506 may store other types of content or data (e.g., machine learning models, artificial neural networks, deep neural networks, etc.) that can be processed by the processor 504 to carry out the various method and features described herein. Thus, although various contents of memory 506 may be described as instructions, it should be appreciated that functionality described herein can be achieved through use of instructions, algorithms, and/or machine learning models. The data, algorithms, and/or instructions may cause the processor 504 to manipulate data stored in the memory 506 and/or received from or via the system 512, the database 530, and/or the cloud 534.

The computing device 502 may also comprise a communication interface 508. The communication interface 508 may be used for receiving data (for example, data from an electrode device 518 capable of recording data) or other information from an external source (such as the system 512, the database 530, the cloud 534, and/or any other system or component not part of the system 500), and/or for transmitting instructions, images, or other information to an external system or device (e.g., another computing device 502, the system 512, the database 530, the cloud 534, and/or any other system or component not part of the system 500). The communication interface 508 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 508 may be useful for enabling the device 502 to communicate with one or more other processors 504 or computing devices 502, whether to reduce the time needed to accomplish a computing-intensive task or for any other reason.

The computing device 502 may also comprise one or more user interfaces 510. The user interface 510 may be or comprise a keyboard, mouse, trackball, monitor, television, screen, touchscreen, and/or any other device for receiving information from a user and/or for providing information to a user. The user interface 510 may be used, for example, to receive a user selection or other user input regarding any step of any method described herein. Notwithstanding the foregoing, any required input for any step of any method described herein may be generated automatically by the system 500 (e.g., by the processor 504 or another component of the system 500) or received by the system 500 from a source external to the system 500. In some embodiments, the user interface 510 may be useful to allow a surgeon or other user to modify instructions to be executed by the processor 504 according to one or more embodiments of the present disclosure, and/or to modify or adjust a setting of other information displayed on the user interface 510 or corresponding thereto.

Although the user interface 510 is shown as part of the computing device 502, in some embodiments, the computing device 502 may utilize a user interface 510 that is housed separately from one or more remaining components of the computing device 502. In some embodiments, the user interface 510 may be located proximate one or more other components of the computing device 502, while in other embodiments, the user interface 510 may be located remotely from one or more other components of the computer device 502.

Though not shown, the system 500 may include a controller, though in some embodiments the system 500 may not include the controller. The controller may be an electronic, a mechanical, or an electro-mechanical controller. The controller may comprise or may be any processor described herein. The controller may comprise a memory storing instructions for executing any of the functions or methods described herein as being carried out by the controller. In some embodiments, the controller may be configured to simply convert signals received from the computing device 502 (e.g., via a communication interface 508) into commands for operating the system 512 (and more specifically, for actuating the implantable pulse generator 516 and/or the electrode device 518). In other embodiments, the controller may be configured to process and/or convert signals received from the system 512. Further, the controller may receive signals from one or more sources (e.g., the system 512) and may output signals to one or more sources.

The database 530 may store information such as patient data, results of a stimulation and/or blocking procedure, stimulation and/or blocking parameters, current parameters, electrode parameters, etc. The database 530 may be configured to provide any such information to the computing device 502 or to any other device of the system 500 or external to the system 500, whether directly or via the cloud 534. In some embodiments, the database 530 may be or comprise part of a hospital image storage system, such as a picture archiving and communication system (PACS), a health information system (HIS), and/or another system for collecting, storing, managing, and/or transmitting electronic medical records.

The cloud 534 may be or represent the Internet or any other wide area network. The computing device 502 may be connected to the cloud 534 via the communication interface 508, using a wired connection, a wireless connection, or both. In some embodiments, the computing device 502 may communicate with the database 530 and/or an external device (e.g., a computing device) via the cloud 534.

The system 500 or similar systems may be used, for example, to carry out one or more aspects of any of the methods 300 and/or 400 as described herein. The system 500 or similar systems may also be used for other purposes.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for stimulating an anatomical element of a patient, comprising:

an implantable pulse generator configured to generate a current;

an electrode device electrically coupled to the implantable pulse generator, the electrode device comprising a plurality of cuff electrodes configured for placement around the anatomical element of the patient, wherein the anatomical element of the patient comprises a posterior sub diaphragmatic celiac vagal trunk and an anterior sub diaphragmatic hepatic vagal trunk;

a monitoring device configured to monitor glucose levels in the patient;

a processor; and a memory storing data for processing by the processor, the data, when processed, causes the processor to:

in response to the monitored glucose levels falling below a threshold value:

transmit instructions to the implantable pulse generator to apply the current to the posterior sub diaphragmatic celiac vagal trunk via a first cuff electrode to downregulate neural activity of the posterior sub diaphragmatic celiac vagal trunk; and transmit instructions to the implantable pulse generator to apply the current to the anterior sub diaphragmatic hepatic vagal trunk via a second cuff electrode to upregulate neural activity of the anterior sub diaphragmatic hepatic vagal trunk, wherein downregulating neural activity of the posterior sub diaphragmatic celiac vagal trunk and upregulating neural activity of the anterior sub diaphragmatic hepatic vagal trunk reduces insulin production by the patient's pancreas.

2. The system of claim 1, wherein the current applied to the anatomical element of the patient results in an increase in blood sugar levels of the patient.

3. A system for stimulating an anatomical element of a patient, comprising:

an implantable pulse generator configured to generate a current;

an electrode device comprising:

a body; and a plurality of cuff electrodes configured for placement around the anatomical element, and configured to apply the current to the anatomical element;

a monitoring device configured to monitor glucose levels in the patient;

a processor; and a memory storing data for processing by the processor, the data, when processed, causes the processor to:

in response to the monitored glucose levels falling below a threshold value:

transmit instructions to the implantable pulse generator to apply the current to the posterior sub diaphragmatic celiac vagal trunk via a first cuff electrode to downregulate neural activity of the posterior sub diaphragmatic celiac vagal trunk; and transmit instructions to the implantable pulse generator to apply the current to the anterior sub diaphragmatic hepatic vagal trunk via a second cuff electrode to upregulate neural activity of the anterior sub diaphragmatic hepatic vagal trunk, wherein downregulating neural activity of the posterior sub diaphragmatic celiac vagal trunk and upregulating neural activity of the anterior sub diaphragmatic hepatic vagal trunk reduces insulin production by the patient's pancreas.

4. The system of claim 3, wherein the current applied to anatomical element of the patient results in an increase in blood sugar levels of the patient.

5. A system for regulating insulin production in a patient, comprising:

an implantable pulse generator configured to generate a current;

an electrode device electrically coupled to the implantable pulse generator, the electrode device comprising a plurality of cuff electrodes;

a first cuff electrode of the plurality of cuff electrodes configured for placement around a posterior sub diaphragmatic celiac vagal trunk of the patient, wherein the current generated by the implantable pulse generator is applied to the posterior sub diaphragmatic celiac vagal trunk via the first cuff electrode to downregulate neural activity of the posterior sub diaphragmatic celiac vagal trunk;

a second cuff electrode of the plurality of cuff electrodes configured for placement around an anterior sub diaphragmatic hepatic vagal trunk of the patient, wherein the current generated by the implantable pulse generator is applied to the anterior sub diaphragmatic hepatic vagal trunk via the second cuff electrode to upregulate neural activity of the anterior sub diaphragmatic hepatic vagal trunk, and wherein downregulating neural activity of the posterior sub diaphragmatic celiac vagal trunk and upregulating neural activity of the anterior sub diaphragmatic hepatic vagal trunk reduces insulin production by the patient's pancreas; and a monitoring device configured to monitor glucose levels in the patient, wherein the current from the implantable pulse generator is applied when the monitored glucose levels fall below a threshold value.

* * * * *